United States Patent [19]

Verter

[11] 4,446,858
[45] May 8, 1984

[54] ARM AND SHOULDER BRACE

[76] Inventor: Allan H. Verter, 684 Franklin Ave., Nutley, N.J. 07110

[21] Appl. No.: 392,560

[22] Filed: Jun. 28, 1982

[51] Int. Cl.³ .............................................. A61F 5/40
[52] U.S. Cl. .................................................... 128/94
[58] Field of Search ..................... 128/77, 78, 94, 158, 128/88, DIG. 19, 87 R

[56] References Cited

U.S. PATENT DOCUMENTS

| 2,415,288 | 2/1947 | Jordon | 128/88 |
| 3,548,818 | 12/1970 | Kaplan | 128/78 |
| 4,198,964 | 4/1980 | Honneffer | 128/87 R |

FOREIGN PATENT DOCUMENTS 1147711 4/1963 Fed. Rep. of Germany ........ 128/88
488427 10/1918 France ................................ 128/94

Primary Examiner—Richard J. Apley
Assistant Examiner—Harry Macey
Attorney, Agent, or Firm—M. K. Silverman

[57] ABSTRACT

The disclosed arm and shoulder brace employs a rigid U-shaped element adapted in size and dimension for placement above the shoulder and adjacent to the base of the neck of a patient, the external surface of said U-shaped element provided with pressure responsive attachment means. Associated with the U-shaped element are a variety of straps for attachment about the upper arm and upper torso, as well as a sling, whereby through the use of the various straps and bands the shoulder and upper arm may be supported while permitting desired flexibility thereof.

1 Claim, 10 Drawing Figures

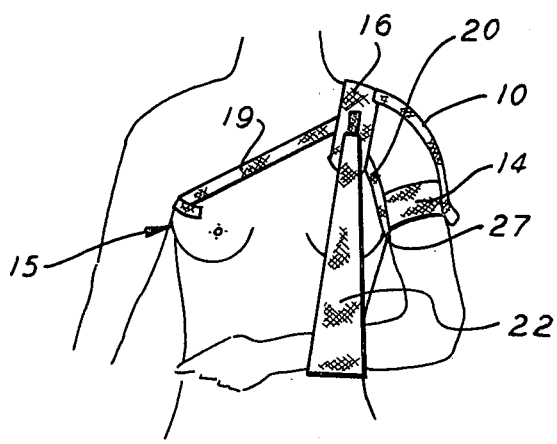
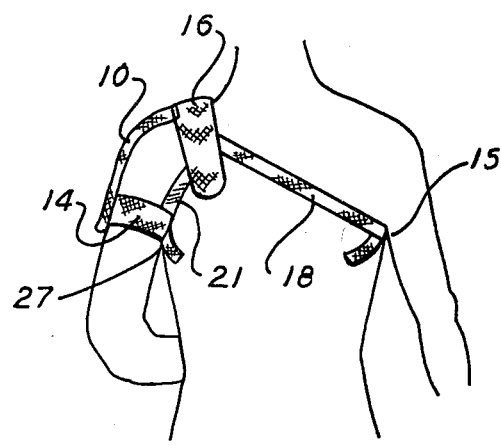
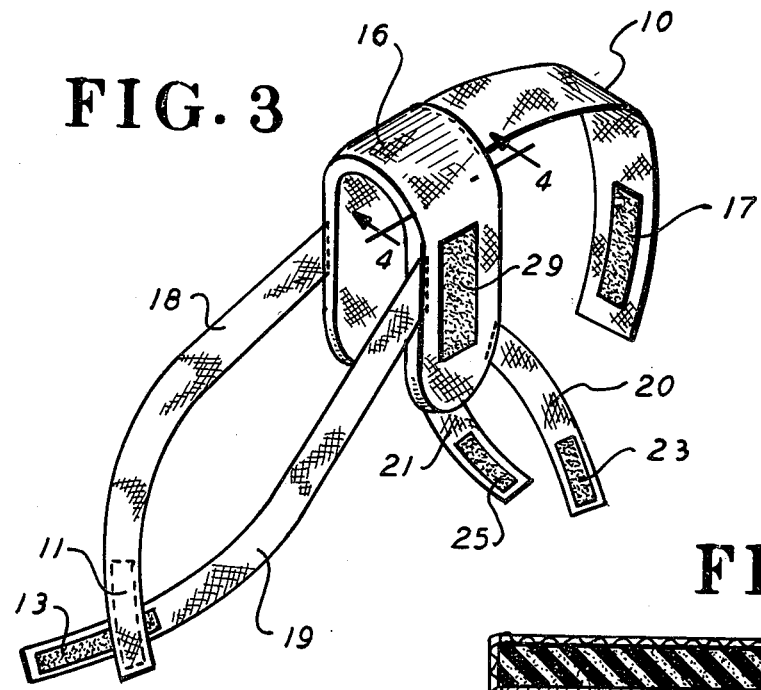
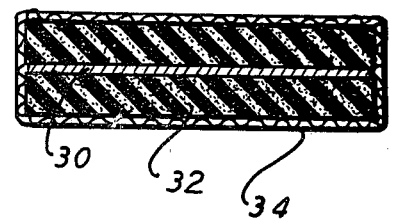

ARM AND SHOULDER BRACE

BACKGROUND OF THE INVENTION

The present invention relates to body supports and binders and, more particularly, to arm and shoulder braces. The present invention is intended to support the shoulder and arm in a manner which is particularly advantageous in certain conditions—namely a stroke or an accident where there is a lack of muscle tone or ligament integrity, or where there is a subluxation or dislocation or some other instability of the shoulder ligaments or muscles resulting from trauma, sprain or strain. In such conditions there may be a hanging-down of the arm such that the weight of the arm itself creates an undesirable stress on the shoulder ligaments and muscles. Accordingly, the present invention is concerned with preventing this weighing-down on the ligaments, supporting tissues and muscles beyond a normal and tolerable amount, while still allowing movement of the shoulder without completely immobilizing the arm, as is the case with a traditional sling. It is also desirable to avoid reliance solely on a sling in that the sling does not totally stop the downward pull of the arm because of its basic function of simply grabbing the forearm and still leaving most of the weight of the arm to overextend the supportive tissue and most of the structures of the shoulder joint itself.

The prior art in the present area is reflected in such patents as U.S. Pat. Nos. 3,182,655; 3,548,818; and 3,554,190, all of which may be found within U.S. Class 128, Sub-class 78.

Neither this prior art, or any other known to the Applicant, provides comparable function or value to a patient.

SUMMARY OF THE INVENTION

The present invention shoulder brace comprises a rigid U-shaped element adapted in size and dimension for placement above the shoulder and adjacent to the base of the neck of a patient, both the external or lateral and internal or medial surfaces of said U-shaped element provided with pressure responsive attachment means; two front straps of unequal length, the lateral being shorter and the medial longer and both having first and second ends, the first ends permanently secured to said U-shaped element at slightly different levels with the lateral strap secured at a point near the beginning of the curved end portion and the medial strap at a point approximately halfway between the curved end and the trough of the rigid U-shaped element, and having at the second ends thereof pressure responsive attachment means; two back straps of unequal length, the lateral being shorter and the medial longer and both having first and second ends, the first ends permanently secured to said U-shaped element at slightly different levels with the lateral strap secured at a point near the beginning of the curved end portion and the medial strap at a point approximately halfway between the curved end and the trough of the rigid U-shaped element, and having at the second ends thereof pressure responsive attachment means, for attachment to said front straps below the wearer's underarm or axillary areas; a surgical band having dimensions suitable for encirclement of the upper bicep, said surgical band having a first end and a second end and, at both ends and on both sides thereof, having pressure responsive attachment means; a deltoid strap having a first end and a second end, said deltoid strap permanently secured at one end to the trough of the rigid U-shaped element and the other end of the deltoid strap provided with pressure responsive attachment means, said pressure responsive attachment adapted for connection to the pressure responsive attachment means upon the exterior of said upper bicep surgical band, whereby the arm of a patient may be supported by encircling the upper bicep with said bicep strap and securing said bicep strap to the U-shaped element by means of said deltoid strap. The use of said pressure responsive attachment means on said straps and bands allows adjustment of dimensions of and pressures exerted by all said straps and bands to degrees suitable for each and any wearer of said brace. Further, the securing of said front and back lateral straps to each other and said front and back medial straps to each other provides lateral stability to the shoulder brace and more specifically to the rigid U-shaped element upon whose stability the deltoid strap relies for said deltoid strap to in turn provide dependable and stable support for injured or other wise weakened muscles or ligaments of the shoulder area against the weight of the arm.

Accordingly, it is an object of the present invention to provide a means for preventing the weighing down or hyperextension of the ligaments, muscles and supporting tissues of the shoulder joint beyond their normal extents, while still allowing movement of the shoulder joint without completely immobilizing the arm.

Yet further objects and advantages will become apparent from the following description of the invention and drawings affixed herewith.

BRIEF DESCRIPTION OF THE DRAWINGS

FIG. 1 is a front perspective view of the improved arm and shoulbrace as actually utilized by a patient.

FIG. 2 is a rear view of the arm and shoulder brace as actually used by a patient.

FIG. 3 is a perspective view of the entire arm and shoulder brace apparatus (excluding the sling).

FIG. 4 is a cross-sectional view taken along line 4—4 of FIG. 3.

DETAILED DESCRIPTION OF THE INVENTION

Figure 5:
FIG. 5 is a plan view of the velcro side of the medial rear strap.

With reference to FIGS. 1 and 2 there is shown a rigid U-shaped element 16 which is adapted to fit over the shoulder at a point abutting the base of the neck of the patient. Affixed to the U-shaped element 16 are a medial front strap 19 (see FIG. 1), a medial back strap 18 (see FIG. 2), a lateral front strap 20 (see FIG. 1) and a lateral rear strap 21 (see FIG. 2). These straps are secured to each other through the use of velcro attachments means 11 and 13 for the medial straps and 23 and 25 for the lateral straps (see FIGS. 3, 5, 6 and 7). The connection of velcro elements 11, 13, 23 and 25 occurs underneath the armpits 15 and 27 respectively (see FIG. 2) of the patient and serve to provide the present shoulder brace with appropriate lateral support.

There is also provided an upper bicep band 14 which encircles the user's upper bicep and is connected to the U-shaped element 16 by means of a shoulder deltoid support element 10 (see FIGS. 1, 2 and 3). Said element 10 is connected to the upper bicep band 14 through the use of velcro element 17 which secures the deltoid band 10 to the bicep band 14.

The U-shaped element 16 is also provided with velcro element 29 to which a sling 22 is connected (see FIGS. 1 and 3).

Figure 6:
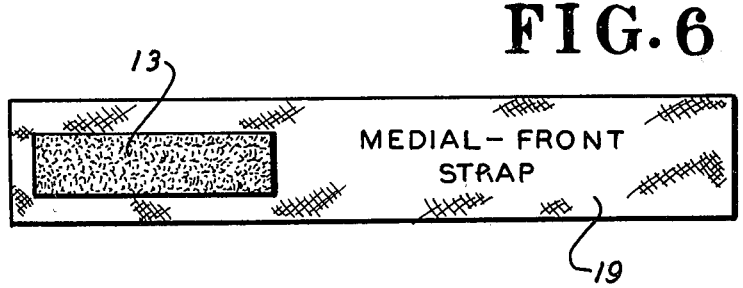
FIG. 6 is a plan view of the velcro side of the medial front strap.
Figure 7:
FIG. 7 is a plan view of the velcro side of the lateral front or lateral rear straps—both of these straps being identical in dimension and form.
Figures 8, 9:
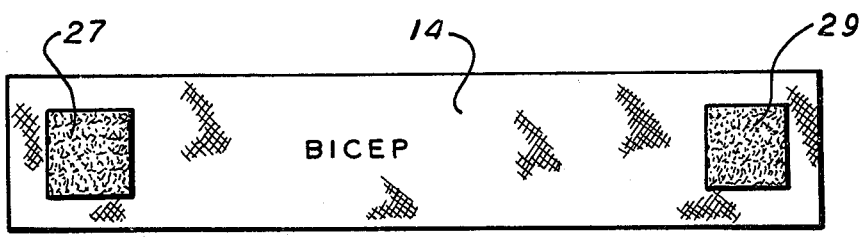
FIG. 8 is a plan view of the velcro side of the bicep strap used in association with the present shoulder brace.
FIG. 9 is a longitudinal side view of the arm band of FIG. 8.
Figure 10:
FIG. 10 is a plan view of the velcro side of the sling which is used in association with the present shoulder brace.

Each of the elements associated with the present shoulder brace are shown in plan view in FIGS. 5 through 10; more particularly, the medial rear band 18 is shown in FIG. 5, the medial front band 19 in FIG. 6, the lateral front and lateral rear straps in FIG. 7, the bicep band 14 in FIG. 8, and the sling 22 in FIG. 10. Also shown, in FIG. 9, is a side plan view of the bicep band 14. In FIG. 9, the presence of velcro on both sides of the bicep band is illustrated.

With reference to FIG. 4, which is a cross-sectional view of the U-shaped element 16 taken along line 4—4 of FIG. 3, the constituent parts of the U-shaped element 16 can be seen. In particular, it is noted that the U-shaped element comprises a metal substrate 30, a thick layer of padding 32, and a thin muslin exterior surface which is intended for contact with the patient's skin.

With respect to the operation of the present shoulder brace, the bicep band 14 and the deltoid strap 10 serve as the basic means for supporting the user's arm and become the means by which the arm is held more closely and thereby sufficiently supported into the shoulder socket of the user. The use of velcro permits adjustability of the amount of pull or pressure against the arm. Such adjustability is desirable for at least two reasons:

The first is that of the different anatomical lengths of each person with whom the brace might be used; the second is that the use of velcro allows for different extents of drawing of the arm into the shoulder socket depending upon the amount of dislocation or instability of the ligaments, this depending on the degree of severity of the condition of the user. For example, the degree of stretch or overstretch of a joint or a muscle, the tolerability of the patient to the otherwise correct amount of pull-back into the shoulder joint, and other reasons, all have indicated a need for a shoulder brace having both lengths and pressures which can be varied in dependence upon any and all circumstances of the patient.

The velcro attachments 13 and 11 of medial front and medial rear straps 19 and 18 respectively, and the velcro attachments 23 and 25 of the lateral front and lateral rear straps 20 and 21 respectively, permit the U-shaped element or the shoulder portion of the brace to be adjusted and secured upon any patient regardless of the dimensions of the patient's chest wall.

It is also to be noted that the position at which the front strap 19 is connected with reference to the U-shaped element 16 is such that the strap 19 will not cause pressure or discomfort upon the breast area.

The sling 22 serves the conventional purpose of supporting the forearm. However, by virtue of the velcro element 29 of the U-shaped element 16, connection with velcro element 31 of the sling 22 can be effectuated so as to easily vary the angle at which the forearm is supported with reference to the torso.

While there have been shown and described the preferred embodiments of the present invention, it will be understood that the invention may be embodied otherwise then is herein specifically illustrated or described and that within said embodiments certain changes in the detail and construction, and the form and arrangement of the parts, may be made without departing from the underlying idea or principle of this invention within the scope of the appended claims.

Having thus described my invention what I claim as new, useful and non-obvious and accordingly secure by Letters Patent of the United States is:

1. An arm and shoulder brace, comprising:
   (a) a rigid U-shaped element having a trough portion with first and second leg portions terminating in a substantially spaced parallel relationship, said U-shaped element adapted in size and dimension for placement above the shoulder and adjacent to the base of the neck of a patient, the external surface of said U-shaped element provided with pressure responsive attachment means;
   (b) two lateral straps having first ends and second ends each, the first ends permanently secured to said U-shaped element at points near the beginning of each of the leg portions thereof, the second lateral strap ends extending downwardly from the leg portions, and having at the second ends thereof pressure responsive attachments means;
   (c) two medial straps having first and second ends each, the first ends permanently secured to said U-shaped element at points approximately half way between the leg portions and the trough of said U-shaped element the second medial strap ends extending laterally outwardly from the trough portion, and the second ends thereof being provided with pressure responsive attachment means;
   (d) a surgical bicep band having dimensions suitable for encirclement of the upper bicep, said surgical band having a first end and a second end, and at both ends and on both sides thereof, having pressure responsive attachments means;
   (e) a deltoid strap having a first end and a second end, said deltoid strap permanently secured at one end to the trough of the rigid U-shaped element and extending downwardly therefrom, and the other end of the deltoid strap provided with pressure responsive attachment means adapted for securement to the bicep band side pressure responsive attachment means; and
   (f) a sling having a first end and a second end, each of said ends provided with pressure responsive attachments means, and each said pressure responsive attachment adapted for connection to the pressure responsive attachment means upon the exterior of the U-shaped element, whereby the muscles and ligaments of a patient may be supported by encircling the upper bicep with said bicep band and securing said bicep band to the U-shaped element by means of said deltoid strap, through the connection of said deltoid strap to the upper bicep band using said pressure responsive attachment means of the respective bicep band and deltoid strap in order to facilitate effective adjustment of the bicep band and deltoid strap to provide suitable pressures by the respective bicep band and deltoid strap against the injured muscles or ligaments of the shoulder area, and further whereby, said medial and lateral straps may be secured under the armpits of the user, this providing lateral stability to the U-shaped element of the brace.

* * * * *